United States Patent
Seemann et al.

(10) Patent No.: US 12,303,112 B2
(45) Date of Patent: *May 20, 2025

(54) RETRACTION SYSTEMS, ASSEMBLIES, AND DEVICES

(71) Applicant: Mazor Robotics Ltd., Caesarea (IL)

(72) Inventors: Ziv Seemann, Beit Ytzhack (IL); Dor Kopito, Kibbutz Parod (IL); Jaffar Hleihil, Zichron Yaakov (IL); Nimrod Dori, Atlit (IL); Ron Visbrot, Hadera (IL)

(73) Assignee: Mazor Robotics Ltd., Caesarea (IL)

( * ) Notice: Subject to any disclaimer, the term of this patent is extended or adjusted under 35 U.S.C. 154(b) by 20 days.

This patent is subject to a terminal disclaimer.

(21) Appl. No.: 18/213,121

(22) Filed: Jun. 22, 2023

(65) Prior Publication Data
US 2023/0329543 A1  Oct. 19, 2023

Related U.S. Application Data

(63) Continuation of application No. 17/590,945, filed on Feb. 2, 2022, now Pat. No. 11,723,528.

(51) Int. Cl.
*A61B 1/32* (2006.01)
*A61B 17/02* (2006.01)

(52) U.S. Cl.
CPC ............ *A61B 1/32* (2013.01); *A61B 17/0206* (2013.01)

(58) Field of Classification Search
CPC .............................. A61B 1/32; A61B 17/0206
USPC .................................................. 600/201–245
See application file for complete search history.

(56) References Cited

U.S. PATENT DOCUMENTS

| | | | |
|---|---|---|---|
| 5,158,552 A | 10/1992 | Borgia et al. | |
| 7,540,875 B2 | 6/2009 | Jessen | |
| 11,723,528 B1* | 8/2023 | Seemann | A61B 90/06 600/201 |

(Continued)

FOREIGN PATENT DOCUMENTS

| | | |
|---|---|---|
| EP | 1974679 | 10/2008 |
| WO | WO 2010/073134 | 7/2010 |

(Continued)

OTHER PUBLICATIONS

International Search Report and Written Opinion for International (PCT) Patent Application No. PCT/IL2023/050070, dated May 8, 2023, 16 pages.

(Continued)

*Primary Examiner* — Eduardo C Robert
*Assistant Examiner* — Tara Rose E Carter
(74) *Attorney, Agent, or Firm* — Sheridan Ross P.C.

(57) ABSTRACT

Retraction systems, assemblies, and devices for retracting an end unit are provided. A retraction assembly may be configured to move the end unit of a robot between a first state and a second state. A first signal may be received indicating a working condition. A first instruction may be generated to move the end unit from the second state to the first state. The retraction assembly may be caused to move the end unit from the second state to the first state based on receiving the first signal and the first instruction. The end unit may be held in the first state when the first signal is being received and the retraction assembly may move the end unit from the first state to the second state when the first signal is not received.

20 Claims, 4 Drawing Sheets

(56) References Cited

U.S. PATENT DOCUMENTS

| | | |
|---|---|---|
| 2011/0234141 A1 | 9/2011 | Kataoka |
| 2012/0211006 A1 | 8/2012 | Grill et al. |
| 2015/0182295 A1* | 7/2015 | Bozung .............. A61B 17/1675 623/23.51 |
| 2020/0367989 A1 | 11/2020 | Bono et al. |
| 2020/0405416 A1* | 12/2020 | Shelton, IV ........... A61B 34/20 |
| 2023/0240780 A1 | 8/2023 | Dori et al. |

FOREIGN PATENT DOCUMENTS

| | | |
|---|---|---|
| WO | WO 2018/006046 | 1/2018 |
| WO | WO 2018/101265 | 6/2018 |
| WO | WO 2020/145821 | 7/2020 |
| WO | WO 2021/234930 | 11/2021 |
| WO | WO 2021/258113 | 12/2021 |

OTHER PUBLICATIONS

Official Action for U.S. Appl. No. 17/590,945, dated Dec. 7, 2022, 13 pages.
Notice of Allowance for U.S. Appl. No. 17/590,945, dated Mar. 21, 2023, 5 pages.

* cited by examiner

RETRACTION SYSTEMS, ASSEMBLIES, AND DEVICES

CROSS-REFERENCE TO RELATED APPLICATIONS

This application is a continuation of U.S. application Ser. No. 17/590,945, filed on Feb. 2, 2022, which application is incorporated herein by reference in its entirety.

BACKGROUND

The present disclosure is generally directed to retraction systems, assemblies, and devices, and relates more particularly to retraction systems, assemblies, and devices for retracting an end unit of a robot.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A retraction system according to at least one embodiment of the present disclosure comprises a retraction assembly configured to move an end unit of a robot between a first state and a second state; a processor; and a memory storing data for processing by the processor, the data, when processed, causes the processor to: receive a first signal indicating a working condition that correlates to the end unit in condition for use; generate a first instruction to move the end unit from the second state to the first state; and cause the retraction assembly to move the end unit from the second state to the first state based on receiving the first signal indicating the working condition and the first instruction; wherein the end unit is held in the first state when the first signal is being received and the retraction assembly moves the end unit from the first state to the second state when the first signal is not received.

Any of the aspects herein, wherein the end unit is extended from the robot when in the first state and retracted towards the robot when in the second state.

Any of the aspects herein, wherein the working condition comprises the retraction assembly receiving power from a power source.

Any of the aspects herein, wherein the memory store further data for processing by the processor that, when processed, causes the processor to: receive a second signal indicating a retracting condition; generate a second instruction to move the end unit from the first state to the second state; and cause the retraction assembly to move the end unit from the first state to the second state based on the retracting condition.

Any of the aspects herein, wherein the retracting condition comprises an applied force measured at the end unit meeting or exceeding a force threshold.

Any of the aspects herein, wherein the retraction assembly comprises an electric coil configured to move the end unit between the first state and the second state and a biasing member configured to exert a biasing force to bias the end unit to the second state.

Any of the aspects herein, wherein the electric coil causes the end unit to extend against the biasing force to move the end unit from the second state to the first state when the electric coil is energized.

Any of the aspects herein, wherein the biasing force moves the end unit from the first state to the second state when the electric coil is not energized.

Any of the aspects herein, wherein the electric coil is configured to be energized in a first condition and a second condition, wherein the electric coil is configured to move the end unit from the first state to the second state when energized in the first condition and wherein the electric coil is configured to move the end unit from the second state to the first state when energized in the second condition.

Any of the aspects herein, wherein the end unit comprises a surgical tool or instrument.

A retraction assembly according to at least one embodiment of the present disclosure comprises a housing configured to receive an end unit; an electric coil configured to move the end unit between a first state and a second state; and a biasing member positioned inside of the housing and configured to exert a biasing force to bias the end unit to the second state, wherein the electric coil causes the end unit to extend against the biasing force to move the end unit from the second state to the first state when the electric coil is energized.

Any of the aspects herein, wherein the housing comprises a stopper configured to stop the end unit from extending past a predetermined distance.

Any of the aspects herein, wherein the end unit extends from the housing when in the first state and retracts inside of the housing when in the second state.

Any of the aspects herein, wherein the biasing member comprises a spring.

Any of the aspects herein, wherein the biasing force moves the end unit from the first state to the second state when the electric coil is not energized.

Any of the aspects herein, wherein the end unit comprises a surgical tool or instrument.

Any of the aspects herein, wherein the electric coil is configured to be energized in a first condition and a second condition, wherein the electric coil is configured to move the end unit from the first state to the second state when energized in the first condition and wherein the electric coil is configured to move the end unit from the second state to the first state when energized in the second condition.

A device for retracting an end unit according to at least one embodiment of the present disclosure comprises a processor; and a memory storing data for processing by the processor, the data, when processed, causes the processor to: receive a first signal indicating a working condition that correlates to an end unit in condition for use; generate a first instruction to move the end unit from the second state to the first state; and cause a retraction assembly to move the end unit from the second state to the first state based on the working condition and the instruction; wherein the end unit is held in the first state when the first signal is being received and the retraction assembly moves the end unit from the first state to the second state when the first signal is not received.

Any of the aspects herein, wherein the working condition comprises the retraction assembly receiving power from a power source.

Any of the aspects herein, wherein the memory store further data for processing by the processor that, when processed, causes the processor to: receive a second signal indicating a retracting condition; generate a second instruction to move the end unit from the first state to the second state; and cause the retraction assembly to move the end unit from the first state to the second state based on the retracting condition.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Surgical robots may be used to perform a surgical procedure autonomously or semi-autonomously such as, for example, cutting a patient with a surgical tool or instrument. During such surgical procedures, it is desirable to protect the patient from unintentional cutting or damage from the surgical tool or instrument. Conventional robots may sag or fall when power is turned off, which may be harmful to a patient if the robot sags towards the patient. In emergency situations, it is undesirable for the robot to fall even a fraction of a mm towards the patient. Further, in some instances a maximum force that the surgical instrument or tool should not exceed during a procedure to prevent excessive force to the patient is known.

In at least one embodiment of the present disclosure, a mechanism such as a retraction assembly for keeping a robot, a robotic arm, an end effector, an end device and/or an end unit such as, for example, a surgical tool or instrument in a working position (such as, for example, a cutting position) when actively actuated is provided. If power is lost to the mechanism, then the end unit is retracted to a safe position. If a force as measured at the end unit is too high, the end unit may be retracted and a user may be alerted of the excessive force. The end unit may be sheathed in a housing so as to protect the end unit and prevent damage to the patient and/or the surgical team by the end unit. Thus, a safer environment is provided to the patient and the surgical team. The mechanism also provides for a robot that is more robust for a surgeon and reduces robotic error e.g., reduces excessive forces and cutting unwanted areas. Further, excessive force mitigation also improves robot accuracy.

Figure 1:
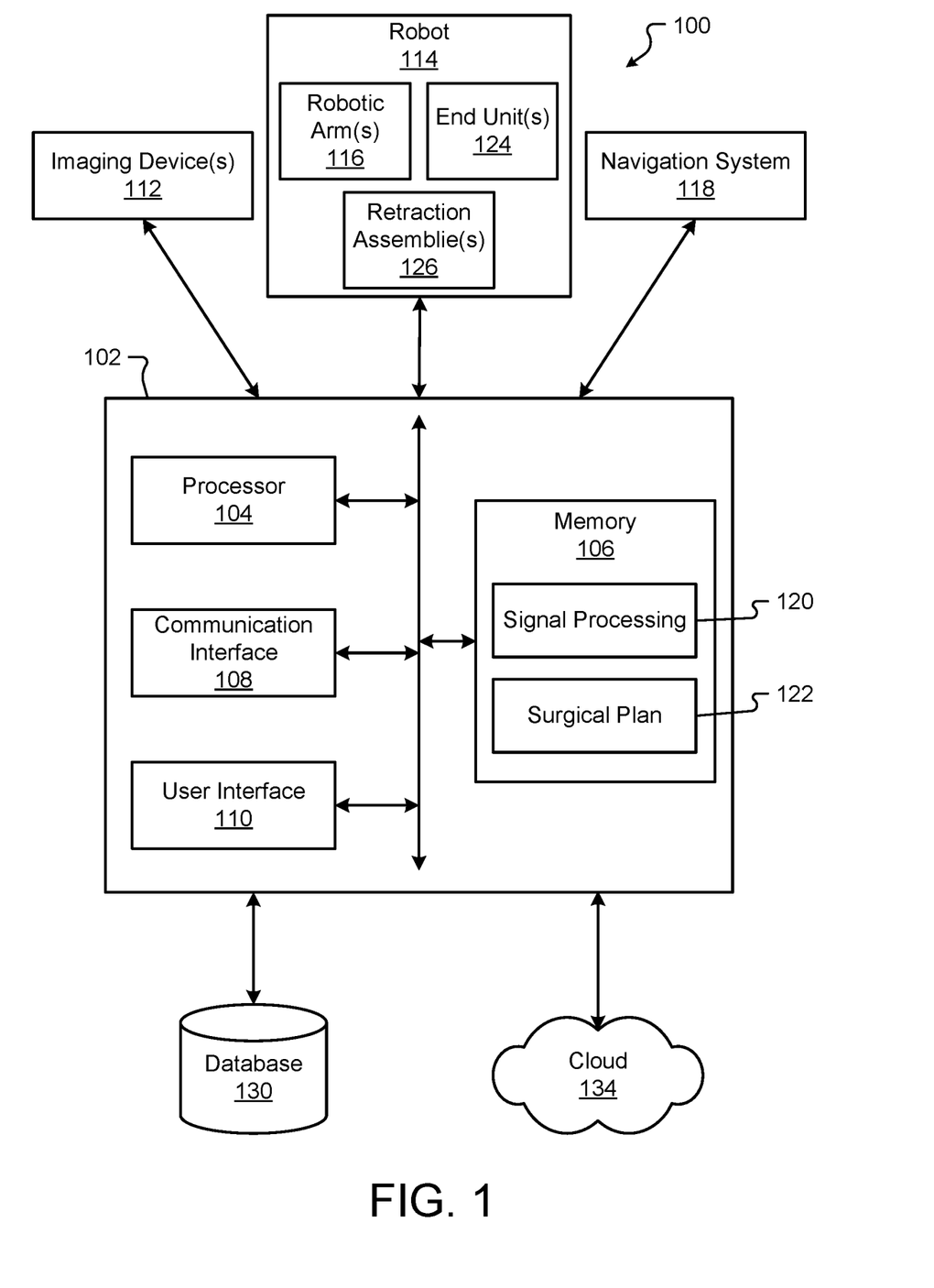
FIG. 1 is a block diagram of a system according to at least one embodiment of the present disclosure.

Embodiments of the present disclosure provide technical solutions to one or more of the problems of (1) preventing an end unit from undesirably contacting a patient, (2) preventing an end unit from applying excessive force to a patient, (3) providing a safety mechanism for autonomous or semi-autonomous surgical robots, (4) increasing patient and surgical team safety, and (5) preventing harm to a patient and/or surgical team from a robot operating with a retraction device Turning first to FIG. 1, a block diagram of a system 100 according to at least one embodiment of the present disclosure is shown. The system 100 may be used to retract an end unit such as an end unit 124, 206 of a robot such as a robot 114 and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 400 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable signal processing 120.

The signal processing 120 enables the processor 104 to process signal data (received from for example, a retraction assembly 126, a power source, the computing device 102, or any component of the system 100 or any component outside of the system 100) for the purpose of, for example, identifying one or more conditions of the retraction assembly 126. The conditions may comprise, for example, a working condition, a retracting condition, a standby condition, or any other condition. The working condition may correlate to whether the end unit 124 is in a working condition and ready for use and may indicate that the end unit 124 is in condition for use. For example, the working condition may indicate that power is received by the end unit 124 of the retraction assembly. The working condition may also indicate activation of, for example, an activation button by a user of the end unit 124. For example, the user may press an activation button and/or maintain a hold on the activation button to maintain the working condition. The activation button may provide an additional safety feature and may prevent the end unit 124 from moving from the second state to the first state and/or being operated unless the activation button is activated. In other words, the end unit 124 may not move from the second state to the first state and/or the end unit 124 may not be operated until the activation button is activated (and in some examples, power is also received by the end unit 124).

The retracting condition may indicate that the end unit 124 is compromised. When the retracting condition is activated, the end unit 124 is retracted towards the robot 114 and away from, for example, a surgical site. The retracting condition may be activated or triggered, for example, a force measured at the end unit meeting or exceeding a force threshold or loss of power to the end unit. The retraction condition may also be activated by a loss of power to the end unit 124. The standby condition may indicate that the end unit 124 is not in use. In the standby condition, the end unit 124 may be retracted towards the robot 114 and into a housing 202 (shown in FIGS. 2, 3A, and 3B) to protect the end unit 124 from damage and/or to prevent damage from the end unit 124 to, for example, a patient or a surgical team.

The content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The memory 106 may also store a surgical plan 122. The surgical plan 122 may comprise, for example, one or more steps for performing a surgical procedure and/or one or more expected thresholds for monitoring one or more parameters during the surgical procedure. For example, the surgical plan 122 may include steps for activating the end unit 124 to put the end unit 124 in the working condition and steps for deactivating the end unit 124 to put the end unit 124 in the standby condition. In some embodiments, the surgical procedure may be a spinal procedure (e.g., a spinal alignment, installing implants, osteotomy, fusion, and/or any other spinal procedure). The surgical plan 122 may also be stored in the database 130.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position, for example, the retraction assembly 126 and the end unit 124 at one or more precise position(s) and orientation(s), and/or to return the retraction assembly 126 and the end unit 124 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the retraction assembly 126 and the end unit 124. In embodiments where two retraction assemblies 126 and end units 124 are used, one robotic arm 116 may hold one set, and another robotic arm 116 may hold another set. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, the retraction assembly 126, the end unit 124, a surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm). The one or more sensors may also measure a force at an end of the robotic arm 116. More specifically, in some embodiments, the sensors may measure a force at an end unit disposed at the end of the robotic arm 116. It will be appreciated that sensors may be used in any other component. For example, a manually operated surgical tool may comprise a retraction assembly 126 and a sensor for measuring a force at the surgical tool. The retraction assembly 126 may be triggered when the sensor measures a force at the surgical tool that meets or exceeds a force threshold.

In some embodiments, reference markers (e.g., navigation markers) may be placed on the robot 114 (including, e.g., on the robotic arm 116), the imaging device 112, the retraction assembly 126, the end unit 124 or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., the retraction assembly 126 and the end unit 124) and the system can operate without the use of the robot 114 (e.g., with the surgeon manually manipulating the retraction assembly 126 and the end unit 124 and/or one or more surgical tools, based on information and/or instructions generated by the navigation system 118, for example).

The robot 114 may also comprise one or more retraction assemblies 126 for moving an end unit 124. The end unit 124 may comprise, for example, a surgical instrument and/or a surgical tool. The retraction assembly 126 may be oriented by, for example, the robotic arm 116. The retraction assembly 126 (and thus the end unit 124) may be positioned at an end of the robotic arm 116 or on any portion of the robot 114 and/or the robotic arm 116. It will be appreciated that in some embodiments, the retraction assembly 126 and the end unit 124 may be manually operated by, for example, a user such as a surgeon or other medical provider. The retraction assembly 126 may be configured to move the end unit 124 from a first state to a second state. It will be appreciated that the retraction assembly 126 may move the end unit 124 to any number of states. In some embodiments, the end unit 124 is extended from the robot 114 when in the first state and the end unit 124 is retracted towards the robot 114 when in the second state. More specifically, and as will be discussed in more detail with respect to FIGS. 2, 3A, and 3B, the end unit 124 may be retracted into a housing 202 so as to cover the end unit 124 and prevent damage from or to the end unit 124 when the end unit 124 is not in use.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the retraction assembly 126, the end unit 124, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans 122 (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

Figure 4:
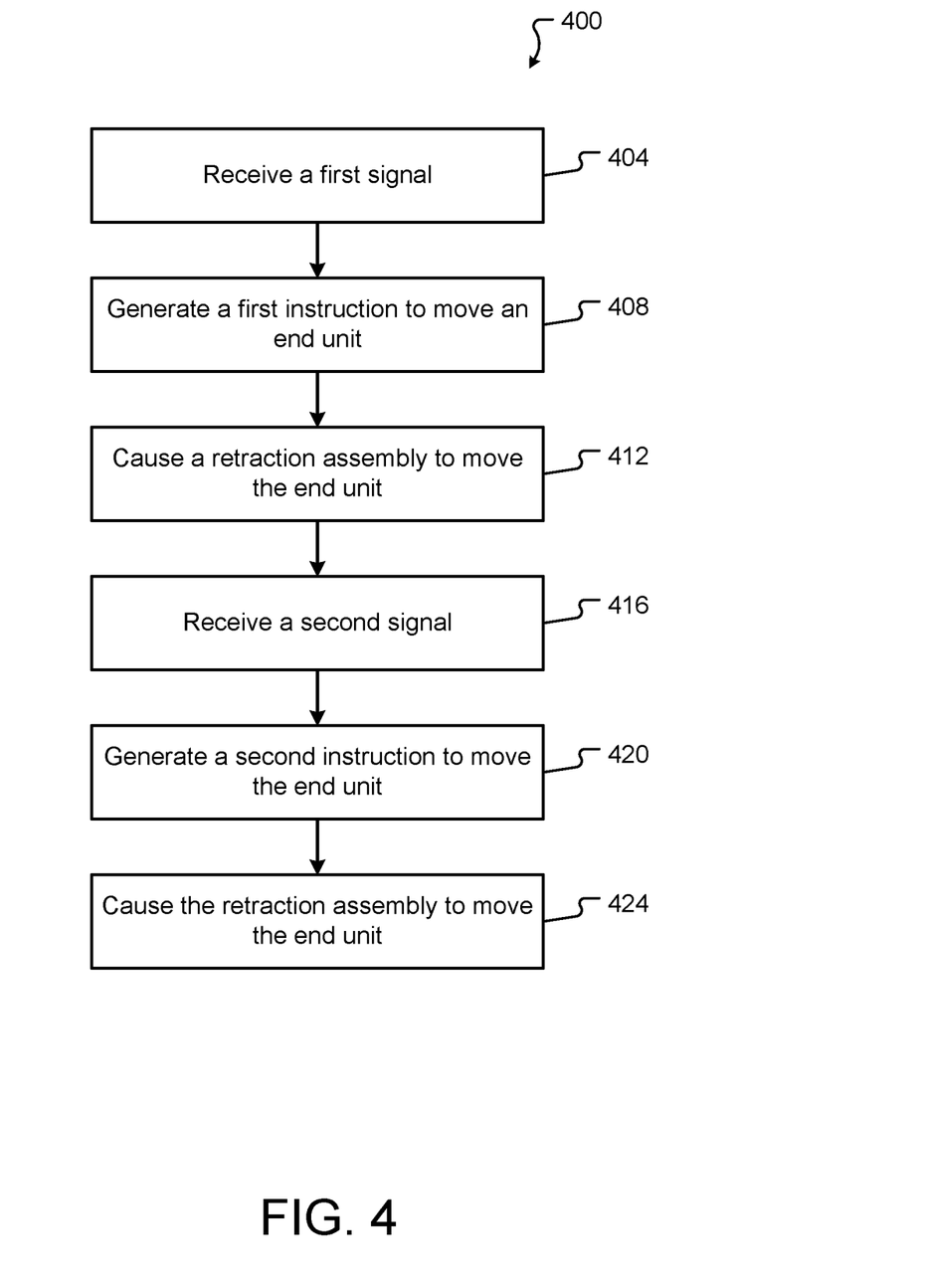
FIG. 4 is a flowchart according to at least one embodiment of the present disclosure.

The system 100 or similar systems may be used, for example, to carry out one or more aspects of any of the method 400 described herein. The system 100 or similar systems may also be used for other purposes.

Figure 2:
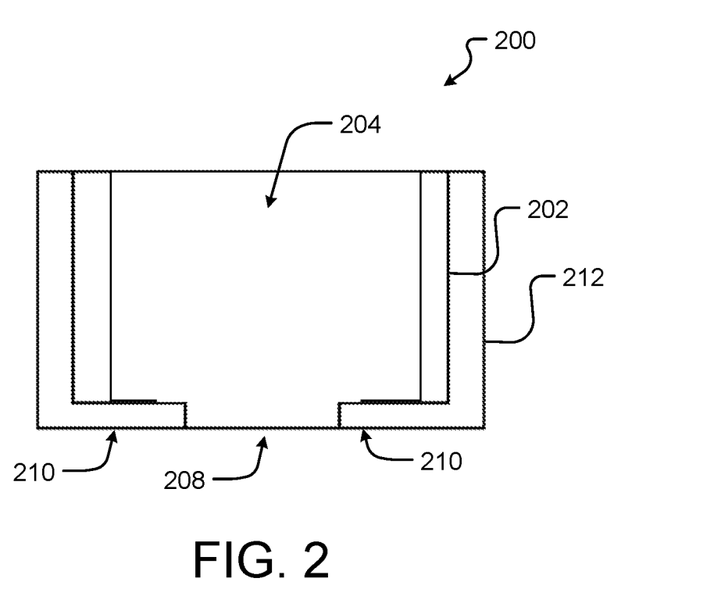
FIG. 2 is a schematic diagram of a retraction assembly according to at least one embodiment of the present disclosure.

FIG. 2 illustrates an example retraction assembly 200. The assembly 200 may be the same as or similar to the assembly 126 described above. The assembly 200 comprises a housing 202 having a cavity 204 for receiving an end unit 206 (shown in FIGS. 3A-3B) and an opening 208 through which the end unit 206 may pass through. The end unit 206 may be the same as or similar to the end unit 124. The assembly 200 may also comprise an electric coil 212 configured to move the end unit 206 between the first state and the second state.

The assembly 200 may also comprise a stopper 210 configured to prevent the end unit 206 from extending past a predetermined distance. The stopper 210 may, in some embodiments, be formed or attached to the electric coil 212. In other embodiments, the stopper 210 may be formed or attached to the housing 202. The stopper 210 may act as a calibrator such that multiple end units 206 may be used and the stopper 210 may prevent each end unit 206 from extending past the same predetermined distance. For example, the end unit 206 may comprise a surgical knife and the surgical knife may become dull during a procedure and may be replaced by a subsequent surgical knife. The stopper 210 may prevent both the initial surgical knife and the subsequent surgical knife from extending past a predetermined distance.

Figure 3A:
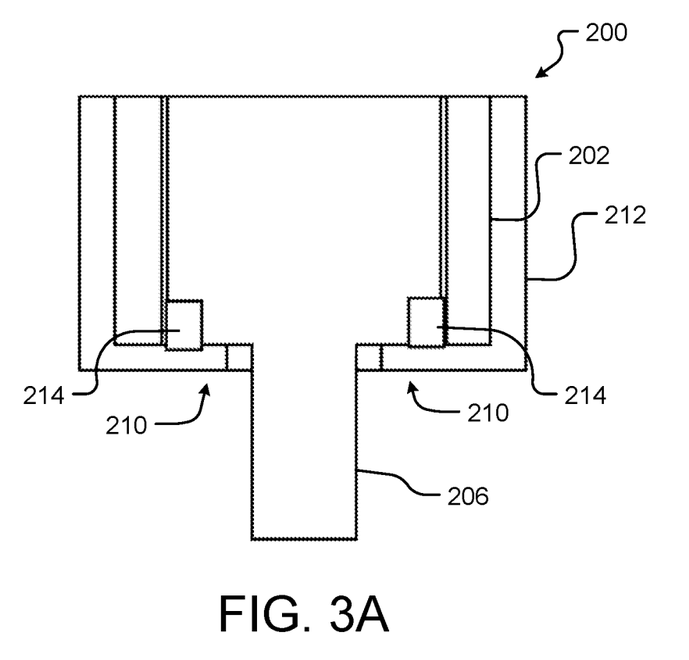
FIG. 3A is a schematic diagram of a retraction assembly in a first state according to at least one embodiment of the present disclosure.
Figure 3B:
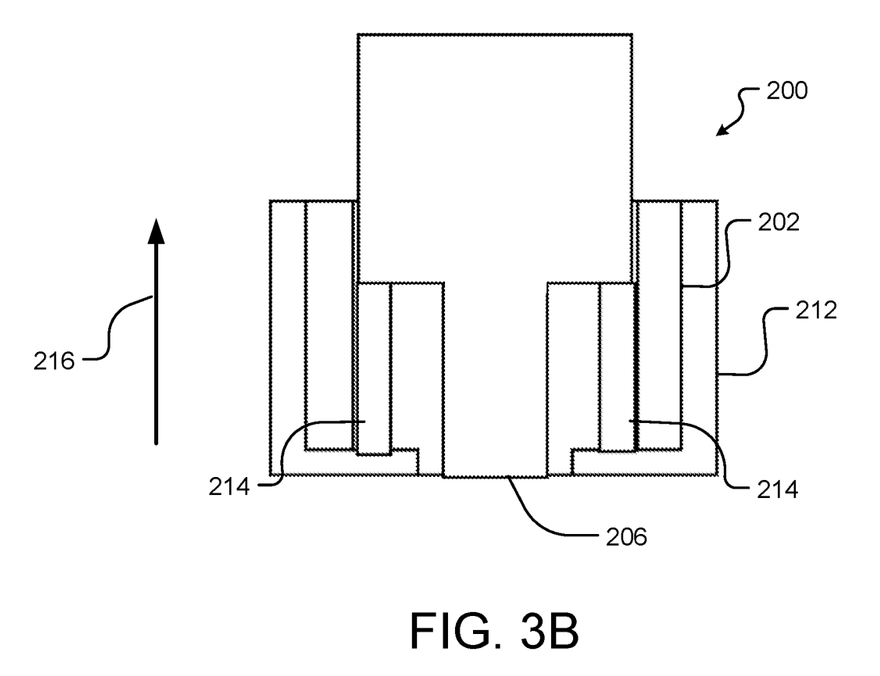
FIG. 3B is a schematic diagram of a retraction assembly in a second state according to at least one embodiment of the present disclosure.

FIGS. 3A and 3B illustrate the retraction assembly 200 in a first state and a second state, respectively. As previously described, the end unit 206 is extended from the robot 114 when in the first state (as shown in FIG. 3A) and the end unit 206 is retracted towards the robot 114 when in the second state (as shown in FIG. 3B). In the illustrated embodiment, the retraction assembly may also include a biasing member 214 positioned inside of the housing 202. The biasing member 214 may be configured to exert a biasing force to bias the end unit 206 to the second state. It will be appreciated that in other embodiments, the biasing member 214 may bias the end unit 206 to the first state, or any state. In such embodiments, the electric coil 212 may cause the end unit 206 to extend against the biasing force to move the end unit 206 from the second state to the first state when the electric coil 212 is energized. Conversely, the biasing force moves the end unit 206 from the first state to the second state when the electric coil is not energized. In some embodiments, the biasing member 214 may be a spring that exerts a spring force.

The electric coil 212 may be configured to be energized in a first condition and a second condition. More specifically, the electric coil 212 may be configured to move the end unit 206 from the first state to the second state when energized in the first condition and configured to move the end unit 206 from the second state to the first state when energized in the second condition. When the electric coil 212 is in the second condition, the electric coil 212 may provide support to the biasing member 214 to move the end unit 206 from the first state to the second state. Such support may be beneficial in, for example, sensitive surgical sites where it may be desirable to remove the end unit 206 from the surgical site as quickly as possible when the end unit 206 is triggered to move from the first state to the second state. For example, it may be desirable to remove an end unit such as, for example, a knife from the surgical site as quickly as possible to prevent accidental damage to tissue at the surgical site.

In embodiments where the electric coil 212 may be energized in the second condition to move the end unit 206 from the first state to the second state, the assembly 200 may not include the biasing member 214. Similarly, in embodiments where the assembly 200 comprises the biasing member 214, the electric coil 212 may not be energized in the second state. In still other embodiments, the electric coil 212 may not be energized when, for example, the assembly 200 is in the standby condition, may be energized in the first condition when the assembly 200 is in the working condition, and may be energized in the second condition when the assembly 200 is in the retracting condition.

When the end unit 206 is retracted and moved to the second state, as shown in FIG. 3B, the biasing force and/or the electric coil 212 may move the end unit 206 in the direction of the arrow 216. Thus, the end unit 206 is retracted into the cavity 204 of the housing 202 and housed to protect the end unit 206 from damage and/or prevent the end unit 206 from causing damage to the surrounding environment.

The end unit 206 may be replaceable and more specifically, the end unit 206 may be removed from and replaced in the housing 202. In some embodiments, the housing 202 and the end unit 206 may be replaced. For example, the housing 202 may be removed and replaced using screws, bolts, or any removable securement feature.

The assembly 200 may be beneficial in providing emergency retraction of an end unit 206 and/or storing an end unit 206 when not in use. For example, in applications where the robotic arm 116 autonomously controls an end unit 206 such as a surgical knife, the robotic arm 116 may fall towards a surgical site if power is unexpectedly lost to the robotic arm 116. The assembly 200 may provide automatic retraction of the surgical knife when power is lost, thereby preventing the surgical knife from damaging the surgical site if the robotic arm 116 drops towards the surgical site. Further, the assembly 200 may provide automatic retraction of, for example, a drill when force measured at the drill at the surgical site exceeds a force threshold, thereby preventing damage to the surgical site by the drill.

FIG. 4 depicts a method 400 that may be used, for example, for moving an end unit using a retraction assembly, system, and/or device.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as a signal processing 120.

The method 400 comprises receiving a first signal (step 404). The first signal may be received from a retraction assembly such as the retraction assembly 126, 200, a power source, a computing device such as the computing device 102, any component of a system such as the system 100, or any component outside of the system. The retraction assembly may be configured to move an end unit such as the end unit 124, 206 from a first state to a second state. In some embodiments, the end unit is extended from a robot such as the robot 114 when in the first state and the end unit is retracted towards the robot when in the second state. More specifically, the retraction assembly may comprise a housing such as the housing 202 into which the end unit is retracted and from which the end unit is extended from. The end unit may be protected in the housing when the end unit is in the second state (e.g., retracted) and may also be prevented from causing damage to a patient (such as, for example, in cases where the end unit is a knife).

The first signal may be received by a processor such as the processor 104. The processor may use, for example, a signal processing such as the signal processing 120 to process the signal data received for the purpose of identifying one or more states of the retraction assembly. In some embodiments, the first signal may indicate a working condition. In other embodiments, the first signal may indicate any one or more conditions such as, for example, a retracting condition or a standby condition.

The working condition may indicate that the end unit is in condition for use. For example, the working condition may indicate that power is received by the end unit of the retraction assembly. The working condition may also indicate activation of, for example, an activation button by a user of the end unit. For example, the user may press an activation button and/or maintain a hold on the activation button to maintain the working condition. The activation button may provide an additional safety feature and may prevent the end unit from moving from the second state to the first state and being used unless the activation button is activated. In other words, the end unit may not move from the second state to the first state until the activation button is activated (and in some examples, power is also received by the end unit).

The method 400 also comprises generating a first instruction to move the end unit (step 408). The first instruction may be generated by, for example, the processor. The first instruction may be generated based on the working condition. In other words, the first instruction may be generated when the first signal is received, indicating that the end unit is in the working condition and ready for use. The first instruction may comprise moving the end unit from the second state to the first state.

The method 400 also comprises causing the retraction assembly to move the end unit (step 412). The retraction assembly may move the end unit from the second state to the first state based on receiving the first signal indicating the working condition and the first instruction.

The assembly may include an electric coil such as the electric coil 212 configured to move the end unit between the first state and the second state. The assembly may also comprise a stopper configured to prevent the end unit from extending past a predetermined distance. The retraction assembly may also include a biasing member such as the biasing member 214 positioned inside of the housing. The biasing member may be configured to exert a biasing force to bias the end unit to the second state. It will be appreciated that in other embodiments, the biasing member may bias the end unit to the first state, or any state. In embodiments where the biasing member biases the end unit to the second state, the electric coil may cause the end unit to extend against the biasing force to move the end unit from the second state to the first state when the electric coil is energized. Conversely, the biasing force moves the end unit from the first state to the second state when the electric coil is not energized. In some embodiments, the biasing member may be a spring that exerts a spring force.

As previously described, the electric coil may be configured to be energized in a first condition and a second condition. More specifically, the electric coil may be configured to move the end unit from the first state to the second state when energized in the first condition and configured to move the end unit from the second state to the first state when energized in the second condition. When the electric coil is in the second condition, the electric coil may provide support to the biasing member to move the end unit from the first state to the second state. Such support may be beneficial in, for example, sensitive surgical sites where it may be desirable to remove the end unit from the surgical site as quickly as possible when the end unit is triggered to move from the first state to the second state. For example, it may be desirable to remove an end unit such as, for example, a knife from the surgical site as quickly as possible to prevent accidental damage to tissue at the surgical site. In embodiments where the electric coil may be energized in the second condition to move the end unit from the first state to the second state, the assembly may not include the biasing member. Similarly, in embodiments where the assembly comprises the biasing member, the electric coil may not be energized in the second state. In still other embodiments, the electric coil may not be energized when, for example, the assembly is in the standby condition, may be energized in the first condition when the assembly is in the working condition, and may be energized in the second condition when the assembly is in the retracting condition.

The method 400 also comprises receiving a second signal (step 416). The step 416 may be the same as or similar to the step 404 described above. The second signal may indicate that the end unit is in a retracting condition and/or a standby condition. The retracting condition may correlate to a condition in which the end unit is compromised and retracted towards the robot 114 and away from a surgical site. The retracting condition may be triggered by, for example, a force measured at the end unit meeting or exceeding a force threshold and/or a loss of power to the end unit.

The force threshold may correlate to a maximum force that an applied force measured at the end unit may not exceed. The force threshold may be determined automatically using artificial intelligence and training data (e.g., historical cases) in some embodiments. In other embodiments, the force threshold may be or comprise, or be based on, surgeon input received via the user interface. In further embodiments, the force threshold may be determined automatically using artificial intelligence, and may thereafter be reviewed and approved (or modified) by a surgeon or other user.

The standby condition may indicate that the end unit is not in use, whether due to the end of a surgical procedure or otherwise. The standby condition may be activated by, for example, a user such as a surgeon or other medical provider. The standby condition may also be automatically activated by, for example, the processor executing a step of a surgical plan such as the surgical plan 122.

The method 400 also comprises generating a second instruction to move the end unit (step 420). The step 420 may be the same as or similar to the step 408 described above. The second instruction may be based on the retracting condition and/or the standby condition. In other words, the second instruction may be generated when the second signal is received, indicating that the end unit is in the retracting condition and/or the standby condition and is not in use. The second instruction may comprise moving the end unit from the first state to the second state.

The method 400 also comprises causing the retraction assembly to move the end unit (step 424). The step 424 may be the same as or similar to the step 412 described above with respect to moving the end unit from the first state to the second state. Moving the end unit from the first state to the second state may be based on receiving the second signal indicating the retracting and/or the standby condition and the second instruction.

In some embodiments, when a force measured at the end unit meets or exceeds a force threshold, the retraction assembly may move the end unit from the first state to the second state and may also generate a notification to a user such as a surgeon or other medical provide. The notification may alert the user that the force at the end unit has met or exceeded the force threshold. The notification may be, for example, an audible sound and/or displayed on a user interface such as the user interface 110.

It will be appreciated that the steps 404-412 and the steps 416-424 may be performed in any order and may be repeated. For example, the steps 416-424 may occur when a force measured at the end unit meets or exceeds a force threshold and the steps 404-412 may then occur when the force does not meet or exceed the force threshold. The steps 416-424 may repeat when the force measured meets or exceeds the force threshold.

In some embodiments, it will be appreciated that the end unit may be held in the first state when the first signal is being received and the retraction assembly may move the end unit from the first state to the second state when the first signal is not received. In other words, in some instances, the end unit may be held in the first state so long as the first signal is continuously received. When the first signal is not received (whether due to, for example, power loss or otherwise), the retraction assembly may automatically move the end unit to the second state.

The present disclosure encompasses embodiments of the method 400 that comprise more or fewer steps than those described above, and/or one or more steps that are different than the steps described above.

As noted above, the present disclosure encompasses methods with fewer than all of the steps identified in FIG. 4 (and the corresponding description of the method 400), as well as methods that include additional steps beyond those identified in FIG. 4 (and the corresponding description of the method 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A retraction assembly comprising:
   a housing configured to receive an end unit; and
   an electric coil configured to move the end unit between a cutting state and a retracting state,
   wherein the electric coil causes the end unit to extend against a biasing force to move the end unit from the retracted state to the cutting state when the electric coil is energized in a first direction, and
   wherein the electric coil exerts a force against the biasing force that is relative to a length of the end unit that is inside of the coil.

2. The retraction assembly of claim 1, further comprising a biasing member positioned inside of the housing and configured to exert the biasing force to bias the end unit to the retracted state.

3. The retraction assembly of claim 2, wherein the biasing member comprises at least one of one or more springs or one or magnets.

4. The retraction assembly of claim 2, wherein the biasing force and an external force experienced by the end unit moves the end unit from the cutting state to the retracted state when the electric coil is not energized, and wherein a speed of the end unit moving from the cutting state to the retracted state is greater when the biasing force and the external force are greater than an expected force.

5. The retraction assembly of claim 2, wherein the biasing force, an external force experienced by the end unit, and the electric coil energized in a second direction to the retracted state moves the end unit from the cutting state to the retracted state, wherein a speed of the end unit moving from the cutting state to the retracted state is greater when the biasing force, the force generated by the electric coil energized in the second direction, and wherein the external force are greater than an expected force.

6. The retraction assembly of claim 1, wherein the end unit extends from the housing when in the cutting state and retracts inside of the housing when in the retracted state.

7. The retraction assembly of claim 1, wherein the end unit comprises a surgical tool or instrument.

8. The retraction assembly of claim 1, wherein the electric coil is configured to be energized in a first condition and a second condition, wherein the electric coil is configured to move the end unit from the cutting state to the retracted state when energized in the first condition, and wherein the electric coil is configured to move the end unit from the retracted state to the cutting state when energized in the second condition.

9. A retraction system comprising:
a retraction assembly having a housing configured to receive an end unit and an electric coil configured to move the end unit between a cutting state and a retracted state, the electric coil configured to cause the end unit to extend against a biasing force to move the end unit from the retracted state to the cutting state when the electric coil is energized, wherein the electric coil exerts a force against the biasing force that is relative to a length of the end unit that is inside of the coil;
a processor; and
a memory storing data for processing by the processor, the data, when processed, causes the processor to:
receive a first signal indicating a working condition that correlates to the end unit in condition for use; and
energize the electric coil to move the end unit from the retracted state to the cutting state based on receiving the first signal indicating the working condition,
wherein the end unit is held in the cutting state when the first signal is being received, and wherein the electric coil moves the end unit from the cutting state to the retracted state when the first signal is not received.

10. The retraction system of claim 9, wherein the retraction assembly further includes a biasing member positioned inside of the housing and configured to exert the biasing force to bias the end unit to the retracted state.

11. The retraction system of claim 10, wherein the biasing member comprises at least one of one or more springs or one or more magnets.

12. The retraction system of claim 10, wherein the biasing force and an external force experienced by the end unit moves the end unit from the cutting state to the retracted state when the electric coil is not energized.

13. The retraction system of claim 9, further comprising a robot configured to support and orient the retraction assembly, wherein the end unit is extended from the robot when in the cutting state and retracted towards the robot when in the retracted state.

14. The retraction system of claim 9, wherein the working condition comprises the retraction assembly receiving power from a power source.

15. The retraction system of claim 9, wherein the memory stores further data for processing by the processor that, when processed, causes the processor to:
receive a second signal indicating a retracting condition; and
cause the retraction assembly to move the end unit from the cutting state to the retracted state based on the retracting condition.

16. A retraction system comprising:
a retraction assembly having an end unit movable between a cutting state and a retracted state, a housing configured to receive the end unit, and an electric coil configured to move the end unit between the cutting state and the retracted state, the electric coil configured to cause the end unit to extend against a biasing force to move the end unit from the retracted state to the cutting state when the electric coil is energized;
a processor; and
a memory storing data for processing by the processor, the data, when processed, causes the processor to:
receive a first signal indicating a working condition that correlates to the end unit in condition for use; and
cause the retraction assembly to move the end unit from the retracted state to the cutting state based on receiving the first signal indicating the working condition,
wherein the end unit is held in the cutting state when the first signal is being received, received and the retraction assembly moves the end unit from the cutting state to the retracted state when the first signal is not received.

17. The retraction system of claim 16, wherein the retraction assembly further includes a biasing member positioned inside of the housing and configured to exert the biasing force to bias the end unit to the retracted state.

18. The retraction system of claim 17, wherein the biasing member comprises at least one of one or more springs or one or more magnets.

19. The retraction system of claim 17, wherein the biasing force and an external force experienced by the end unit moves the end unit from the cutting state to the retracted state when the electric coil is not energized.

20. The retraction system of claim 17, wherein the end unit extends from the housing when in the cutting state and retracts inside of the housing when in the retracted state.

* * * * *